United States Patent [19]

Wilson, Jr. et al.

[11] Patent Number: 4,474,816
[45] Date of Patent: Oct. 2, 1984

[54] CONTROL OF MYCOTOXIN PRODUCTION BY CHEMICALLY INHIBITING FUNGAL GROWTH

[75] Inventors: David M. Wilson, Jr., Tifton; Richard C. Gueldner, Chula, both of Ga.

[73] Assignee: The United States of America as represented by the Secretary of Agriculture, Washington, D.C.

[21] Appl. No.: 539,025

[22] Filed: Oct. 4, 1983

Related U.S. Application Data

[63] Continuation-in-part of Ser. No. 377,509, May 12, 1982, abandoned.

[51] Int. Cl.³ ............................................. A01N 35/00
[52] U.S. Cl. .................................................... 424/331
[58] Field of Search ........................................ 424/331

[56] References Cited

FOREIGN PATENT DOCUMENTS 8173005 6/1981 Japan .

OTHER PUBLICATIONS

Wilson et al., "Effect of B-Ionone on *Aspergillus flavus* and *Aspergillus parasiticus* Growth, Sporulation, Morphology and Aflatoxin Production", JAOCS, Dec. 1981, 959A-961A.

Primary Examiner—Albert T. Meyers
Assistant Examiner—John M. Kilcoyne
Attorney, Agent, or Firm—M. Howard Silverstein; David G. McConnell; Raymond C. Von Bodungen

[57] ABSTRACT

An effective method to control aflatoxin produced by toxic strains of *Aspergillus parasiticus* fungi is disclosed. An effective amount of Beta-ionone is applied to said fungi to inhibit the growth and sporulation of the fungi and thereby control production of aflatoxin from the fungi without killing the fungi.

3 Claims, No Drawings

CONTROL OF MYCOTOXIN PRODUCTION BY CHEMICALLY INHIBITING FUNGAL GROWTH

CROSS REFERENCE TO RELATED APPLICATIONS

This is a continuation-in-part of U.S. application Ser. No. 377,509 filed May 12, 1982 now abandoned.

BACKGROUND OF THE INVENTION (1) Field of the Invention

This invention relates to the control of mycotoxins by means of chemical treatment.

(2) Description of the Prior Art

Heretofore, it has been known that "turkey X" disease has been caused by a toxin produced by some strains of the fungi *Aspergillus parasiticus*. This aflatoxin which is produced by strains of *A. parasiticus* is acutely toxic as well as carcinogenic. However, much of the research on aflatoxin dealt solely with the detection of aflatoxin and relatively little research has been done on the prevention of formation of aflatoxins.

A review of the control or suppression of fungi producing aflatoxin reveals efforts of fumigating with high level dosages of methyl bromide, ethylene dibromide, propane/propene ethylene oxide, sulfur dioxide, and phosphine and did show some effects of fungicidal activity. Ammonia proved to be fungicidal but demonstrated a lack of any residual effect. Propionic, acetic, and isobutyric acids also have antifungal activity. However, all the above chemicals have the definite disadvantage of toxicity to humans and animals, corrosiveness, and lowered nutritional quality. Therefore, they are not acceptable to either humans or animals.

The problem is magnified because fungal invasion of a crop begins in the field and either remains or increases during storage. Thus, levels of aflatoxin usually increase during storage.

SUMMARY OF THE INVENTION

Some strains of *Aspergillus parasiticus* fungi produce serious amounts of aflatoxin in agricultural crops during both preharvest and postharvest periods. This invention consists of a method for inhibiting and controlling said aflatoxin which is produced by aflatoxin producing strains of *aspergillus parasiticus* fungi and comprises: treating the crop and associated fungi with an effective amount of Beta-ionone to inhibit and control the growth and sporulation of said fungi without filling the fungi, and thus eliminate the aflatoxin which would be produced by the fungi is left untreated. Effective amounts of beta-ionone have been determined to be about 1 $\mu$L to 100 $\mu$l.

DESCRIPTION OF THE PREFERRED EMBODIMENTS

*Aspergillus parasiticus* Speare is on deposit with the Agricultural Research Culture Collection (NRRL) in Peoria, Illinois, and has been assigned the following accession number: NRRL 2999. The address of the Agricultural Research Culture Collection (NRRL) is:

A. J. Lyons, Curator, ARS Patent Collection Culture Collection Research NRRC, 1815 N. University Street, Peoria, Ill. 61604.

Beta-ionone has a definite effect on the growth and development of *A. parasiticus* fungi as demonstrated in the following examples:

EXAMPLE 1

*Asperguillus parasiticus* Speare (NRRL 2999)was maintained on potato dextrose agar (pda) slants and used in these experiments. The *A. parasiticus* isolate (NRRL 2999)produces aflatoxins.

Direct contact tests with β-ionone were done using petri dishes (15×100 mm) containing 20 ml pda and maintained at 26° C. Varying amounts (1–20 μl) of β-ionone were pipetted directly onto the pda surface just before inoculation. Some of the cultures were placed in plastic bags during incubation. Gross observations, diameter measurements and microscopic observations were periodically taken.

Bioassays of volatile effects of β-ionone were also done using pda in divided plates. These bioassays were conducted using the following procedure: (a) all 4 quadrants were inoculated with stabs of a spore suspension; (b) different concentrations of β-ionone (1.50 μl) were placed only in 1 quadrant; (c) plates were stored in separate plastic bags and incubated at 26° C.; (d) gross observations and diameter measurements were recorded after 3, 4, or 5 days of incubation; (e) slides were made and microscopic observations recorded.

Shake cultures of *A. parasiticus* (NRRL 2999) were used to determine the effects of β-ionone on growth and aflatoxin production. The medium was prepared by dissolving 50 g Bacto mycological broth w/low pH (Difco), 15 g sucrose and 2 g yeast extract in 1,000 ml $H_2O$. One hundred ml of the medium were placed in 125 ml Erlenmeyer flasks and autoclaved. When the medium was cool, varying amounts of β-ionone (0.100 μl/flask) were pipetted into the flasks. All experiments were replicated at least 4 times. The cultures were inoculated with a spore suspension of *A. parasiticus.* The flasks were sealed with aluminum foil and rubber bands. The cultures were grown on a rotary shaker and dry weights taken at 1,2,3,4,5,6,7, and 10 days.

Aflatoxin was determined from 7-day cultures after extraction of the liquid medium with $CHCl_3$. Twenty-five ml, of medium was removed from each flask and mixed with 25 ml of saturated sodium chloride solution. This mixture was extracted twice with 25 ml $CHCl_3$. The $CHCl_3$ layers were collected and taken to dryness using a rotary evaporator. The residue was suspended in 1 ml $CHCl_3$ then diluted with 1 ml hexane. The suspension was placed on a silica gel Sep-Pak (Water Assoc.) and cluted with 5 ml hexane, 5 ml anhydrous ethyl ether, and 3 ml $CHCl_3/CH_3OH$ (90:10). The $CHCl_3/CH_3OH$ fraction was collected, taken to dryness under $N_2$ and reconstituted in HPLC mobile phase. The aflatoxins were determinied by HPLC using the method of Thean et al.

RESULTS AND DISCUSSIONS

Direct contact of *A. parasiticus* with 1,2.5,5,10,20, and 100 μl of β-ionone placed on the surface of pda resulted in severely restricted growth and arrested sporulation. The colonies remained light brown-white and the growth habit was compact. No sporulation occurred at levels of 5 μl or above even after 4 weeks' incubation. Sporulation occurred after 1–2 weeks with 1 and 2.5 μl of applied β-ionone. These colonies were restricted and many conidial heads were atypical. Frequently, vesicles of reduced size were formed, sometimes with irregular sterigmata. When mycelial fragments from any treatments (1–100 μl) were transferred to fresh pda, normal growth and sporulation ocurred, therefore no fungus was killed.

The volatile effects of β-ionone on opposite or adjacent quadrants were somewhat different than the effects of direct contact. One μl of β-ionone produced effects only in the quadrant containing β-ionone; the growth and sporulation of A. parasiticus was not affected in the other quadrants. In plates with 5,10, 15,20,25,30,35,40,45 and 50 μl β-ionone in 1 quadrant, an increasing effect on growth and sporulation in other quadrants was noted in plates containing 5-20 μl of β-ionone. The effects of increasing from 5 to 20 μl included increasing restriction of colony diameters and decreasing levels of sporulation after 7 days. Radial growth in plates receiving 20-50 μl β-ionone was about half that of the controls. Little sporulation occurred after 7 days in any quadrant of these plates as long as they remained in unopened bags.

Direct contact with β-ionone at levels of 1-20 μl, resulted in very restricted growth, little or no sporulation, and arrested asexual reproductive development. Few, if any, mature conidia were produced. The primary thallus consisted of vegetative hyphae and conidiophore initials that were atypical or of reduced size. The volatile effects of β-ionone were evidenced by morphological changes, growth inhibition, and sporulation reduction in adjaent and opposite quadrants. Microscopic observations included:

Reduced size of vesicle and conidiophore diameter, arrested asexual reproduction with many immature conidiophores; increased vegetative growth when compared to direct contact; atypical distribution of sterigmata, similar to direct contact; elongated, irregular sterigmata; atypical branching of conidiophores and abnormal conidiophore appearance. These effects are concentration-dependent at levels of 1-5 μl/plate for direct contact and at levels of 5-20 μl/plate for volatile effects in divided plates.

The effects of β-ionone on growth (dry wt) and aflatoxin synthesis of A. parasiticus are given in Table 1.

TABLE I

Effects of β-ionone on Growth and Aflatoxin $B_1$
Accumulation In Shake Liquid Cultures of
Aspergillus parasiticus.

| β-Ionone added (μl/l) | Dry wt (g)[b] | Aflatoxin $B_1$ (ng/ml)[b] |
|---|---|---|
| 0 | 1.92 | 9528 |
| 10 | 1.93 | 10200 |
| 50 | 1.50 | 11240 |
| 100 | 1.23 | 2496 |
| 200 | 1.29 | 1568 |
| 250 | 1.02 | 1368 |
| 300 | 0.79 | 176 |
| 400 | 0.84 | 280 |
| 500 | 0.71 | 16 |
| 1000 | 0.74 | 2 |

[b]Numbers are averages from four flasks per treatment

The effects on growth were noticeable beginnin at 50 μl/l of medium. Concentrations above 250 μl/l had little further effect on growth. The primary effect of β-ionone on growth in shake culture seemed to be on the rate of growth; however, sporulation of A. parasiticus in shake or submerged culture is inhibited and was not measured. Concentrations of 100 μl and above of β-ionone/l inhibited aflatoxin accumulations whereas 10 and 50 μl/l slightly stimulated aflatoxin production. This shows that the ability of the toxigenic strain of A. parasiticus to produce aflatoxin is not necessarily linked to growth; but aflatoxin synthesis may be positively correlated with the asexual reproductive process.

We claim:

1. A method for inhibiting aflatoxin which is produced by aflatoxin producing strains of Aspergillus parasiticus fungi, said method comprising: treating the fungi with an effective amount of beta-ionone to inhibit and control the growth and sporulation of said fungi, without killing the fungi, thus eliminating the aflatoxin produced by said fungi.

2. The method of claim 1 wherein the effective amount of beta-ionone is about 1 μl to 100 μl.

3. The method of claim 2 wherein the Aspergillus parasiticus is N